(12) United States Patent
Dervish et al.

(10) Patent No.: US 10,835,180 B2
(45) Date of Patent: Nov. 17, 2020

(54) SENSOR PAD FOR WEARABLE GARMENTS

(71) Applicant: IMPACT TECH LABS AG, Zurich (CH)

(72) Inventors: Kemal Dervish, Welwyn Garden City (GB); Haim Geva, London (GB); Jason Lloyd Roberts, St. Margarets (GB); Giles Hendrick Tongue, West Byfleet (GB)

(73) Assignee: NURVV LIMITED, Twickenham (GB)

( * ) Notice: Subject to any disclaimer, the term of this patent is extended or adjusted under 35 U.S.C. 154(b) by 109 days.

(21) Appl. No.: 15/984,004

(22) Filed: May 18, 2018

(65) Prior Publication Data

US 2018/0333098 A1    Nov. 22, 2018

(30) Foreign Application Priority Data

May 19, 2017    (GB) ..................... 1708073

(51) Int. Cl.
*A61B 5/00*    (2006.01)
*G01L 1/20*    (2006.01)
(Continued)

(52) U.S. Cl.
CPC ............ *A61B 5/6804* (2013.01); *G01L 1/205* (2013.01); *G01L 1/2287* (2013.01);
(Continued)

(58) Field of Classification Search
CPC ..... A61B 5/6804; G01L 1/205; G01L 1/2287; A41C 3/0057; A41D 1/002;
(Continued)

(56) References Cited

U.S. PATENT DOCUMENTS

| 4,527,021 A | 7/1985 | Morikawa et al. |
| 4,602,135 A * | 7/1986 | Phalen ................. H01H 13/702 |
| | | 200/5 A |

(Continued)

FOREIGN PATENT DOCUMENTS

| DE | 4323542 A1 | 1/1995 |
| GB | 2274151 A | 7/1994 |

(Continued)

OTHER PUBLICATIONS

UK Intellectual Property Office, Search Report issued in corresponding Application No. GB1708073.0, dated Oct. 20, 2017.

(Continued)

*Primary Examiner* — Harshad R Patel
*Assistant Examiner* — Nigel H Plumb
(74) *Attorney, Agent, or Firm* — Stites & Harbison, PLLC; Jeffrey A. Haeberlin; Gary N. Stewart (57) ABSTRACT

A sensor pad is provided. The sensor pad comprises a first layer and a second layer of padding material, each having an inner face. The inner face of the first layer is provided with a first printed conductive ink track and the inner face of the second layer is provided with a second printed conductive ink track. At least one of the layers is provided on its inner face with a plurality of raised portions between adjacent runs of the printed track to provide a spacer layer across the sensor pad, which improves the ability of the sensor pad to return to a pre-impact configuration following an impact. The plurality of raised portions maintain the two printed tracks apart when the sensor is unstressed but allow localised contact between the first and second printed tracks when pressure is applied to the sensor pad.

6 Claims, 6 Drawing Sheets

(51) Int. Cl.
*G01L 1/22* (2006.01)
*H05K 1/16* (2006.01)
*H01H 13/703* (2006.01)
*H01H 13/702* (2006.01)
*A41D 13/015* (2006.01)
*H05K 1/03* (2006.01)
*H05K 1/09* (2006.01)
*A41C 3/00* (2006.01)
*H01H 13/704* (2006.01)

(52) U.S. Cl.
CPC ............. *H01H 13/703* (2013.01); *H05K 1/16* (2013.01); *A41C 3/0057* (2013.01); *A41D 13/015* (2013.01); *H01H 13/702* (2013.01); *H01H 13/704* (2013.01); *H01H 2203/0085* (2013.01); *H01H 2207/002* (2013.01); *H01H 2207/01* (2013.01); *H01H 2211/012* (2013.01); *H05K 1/038* (2013.01); *H05K 1/092* (2013.01); *H05K 2201/10151* (2013.01)

(58) Field of Classification Search
CPC .. A41D 31/0058; A41D 31/015; B32B 37/02; B32B 37/12; H01H 13/70
See application file for complete search history.

(56) References Cited

U.S. PATENT DOCUMENTS

| | | | |
|---|---|---|---|
| 4,824,107 A | 4/1989 | French | |
| 5,187,647 A | 2/1993 | Kaneko | |
| 2015/0144248 A1* | 5/2015 | Wu | G01L 1/205 156/64 |
| 2017/0127734 A1* | 5/2017 | Roberts | B32B 5/18 |
| 2017/0127736 A1* | 5/2017 | Roberts | A41D 1/002 |

FOREIGN PATENT DOCUMENTS

| | | |
|---|---|---|
| JP | 2017071862 A | 4/2017 |
| WO | 01/15189 A1 | 3/2001 |
| WO | 2015/014950 A1 | 2/2015 |

OTHER PUBLICATIONS

European Patent Office, Extended European Search Report issued in corresponding Application No. EP 18 17 2590, dated Oct. 15, 2018.

\* cited by examiner

SENSOR PAD FOR WEARABLE GARMENTS

The present invention relates to a sensor pad. In particular, the invention relates to a sensor pad for a wearable garment in order to sense an impact on a body of a user wearing such a pad.

In a wearable garment, particularly one worn on the upper body, a sensor pad is required to cover a relatively large area of the garment as, in many sporting or leisure activities, it is possible that a wearer will receive an impact on any part of the garment. Even for garments such as footwear and headgear, there is a need for a sensor pad which can operate over a wide area. In addition, the pad is required to be flexible as it needs to curve around the contours of the body.

Figure 1:
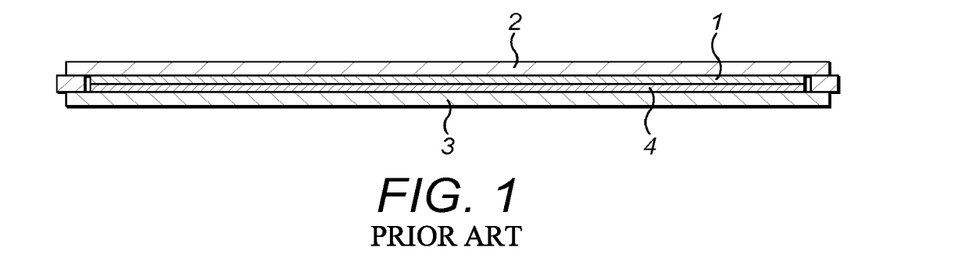
FIG. 1 is a schematic cross-section of a prior art sensor pad.
Figure 2:
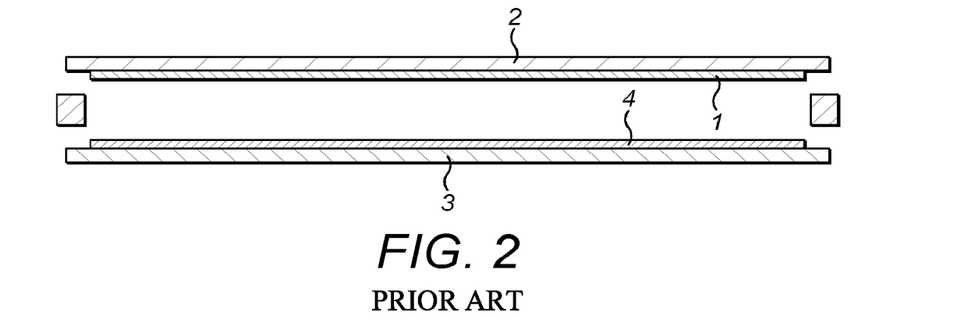
FIG. 2 is a view similar to FIG. 1 showing the sensor pad disassembled.

Existing pressure sensors are generally designed to cover a small area and are generally planar. One example is the ShuntMode matrix array sample produced by Sensitronics LLC (as shown in FIGS. 1 and 2).

Such a sensor consists of a force-sensing resistor ink 1 which is screen printed on one film 2 while the other film 3 is printed with conductive, interdigitated electrode fingers 4. The two films are assembled with the printed surfaces facing each other and are adhered together with spacers around the perimeter.

The present invention is aimed at providing a sensor that can be more readily adapted to the requirements of a wearable garment.

According to the present invention there is provided a sensor according to claim 1.

The present invention effectively spreads the spacer layer across the face of the sensor rather than being around the periphery of the sensor. It is therefore much more readily able to absorb an impact towards the centre of a larger pad and to return the layers to their pre-impact configuration once the force is removed. Also, the sensor can be flexed around more complex shapes while the projections across the inner surface will provide the required support between the layers in any curved region which the peripheral space is unable to do.

Each of the first and second printed conductive ink tracks may be a single track with a connection point at either end. However, such a sensor would be unable to determine information about the location of the impact on the sensor pad. Therefore, preferably, at least one of the printed conductive ink tracks comprises a plurality of discreet tracks.

By having multiple tracks on at least one of the layers, information can be determined about the location of the impact of the pad as the sensor can recognise which of the discreet tracks has received the impact. Both of the first and second printed conductive inks can be provided as multiple discreet tracks as this provides the greatest flexibility in terms of determining the location of the impact. However, this complicates the structure as each individual track requires its own connection point. Therefore, preferably, only one of the printed conductive ink tracks has multiple paths, while the other track has a single sinuous path.

The sensor may further comprise an impact absorbing layer provided on one side of the sensor. The sensor may further comprise an impact dissipating layer within the impact absorbing layer. This layer absorbs and/or distributes any absorbed force across the sensor to reduce any damage to an object the sensor is placed on.

The present invention preferably extends to a wearable garment comprising at least one sensor pad according to the first aspect of the present invention.

Examples of a sensor pad in accordance with the present invention will now be described with reference to the accompanying drawings, in which.

Figure 3:
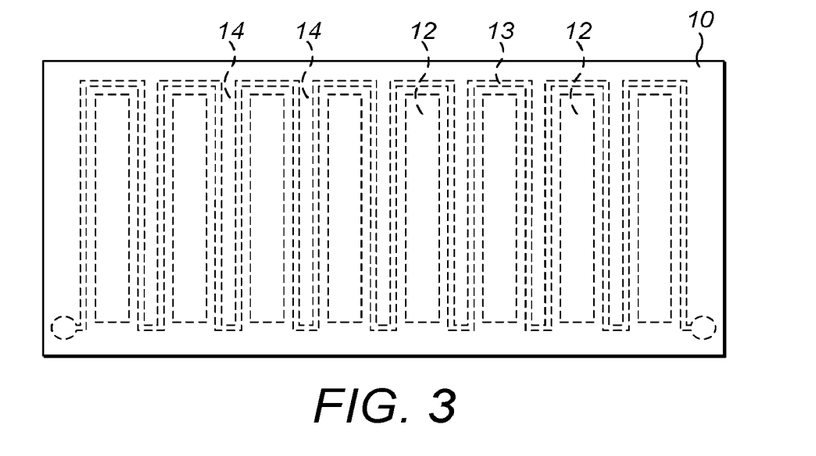
FIG. 3 is a plan view of a layer of a pad according to a first example of the present invention.
Figure 4:
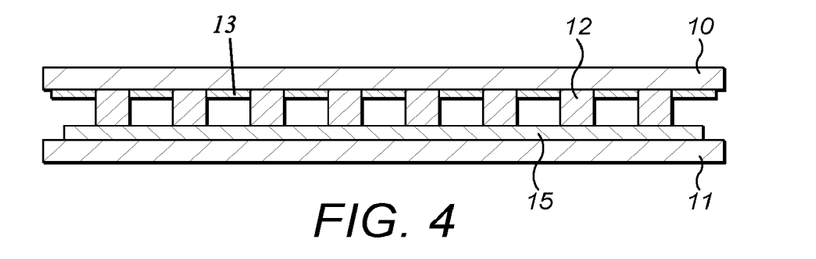
FIG. 4 is a cross-sectional view through a pad of a first example.

As shown in FIGS. 3 and 4, the sensor pad comprises a first layer 10 of a padding material and a second layer 11 of a padding material. The padding material may for example be a thermoplastic polyurethane (TPU) or silicone rubber. The first padding layer 10 is provided with a row of protrusions 12 each being elongate in direction across the pad. The protrusions 12 are arranged in an orthogonal direction along the pad. The important consideration for these protrusions is that they are dispersed across the face of the pad. Thus, they could run across the page in FIG. 3 rather than down the page. Alternatively, each of the elongate protrusions shown here is split up into a number of smaller sections. The protrusions are all shown on a single layer, but could be split across both layers 10, 11.

Between the protrusions 12 is a single printed sinuous conductive track 13 which is connected to the ground which is again required to be spread across the face of the pad. As shown in this example, the track 13 winds around the protrusions 12. As illustrated here, there are two runs of the track between adjacent protrusions 12. However, there could be additional protrusions 12 in the regions 14 between adjacent runs of the track 13.

The second layer 11 is printed with another conductive ink track 15. This should run in a direction generally transverse to the direction of the second conductive ink track 13 to create as many crossing points as possible. The second conductive ink track 15 in FIG. 4 preferably takes the form of a number of discreet tracks with a voltage connected across each one as shown in greater detail in the later examples.

As will be apparent from FIG. 4, the protrusions 12 hold the printed conductive tracks 13, 15 away from one another in an unloaded configuration. When the pad experiences an impact, this causes compression of the protrusions 12 thereby bringing the conductive tracks 13, 15 into contact with one another.

Figure 5:
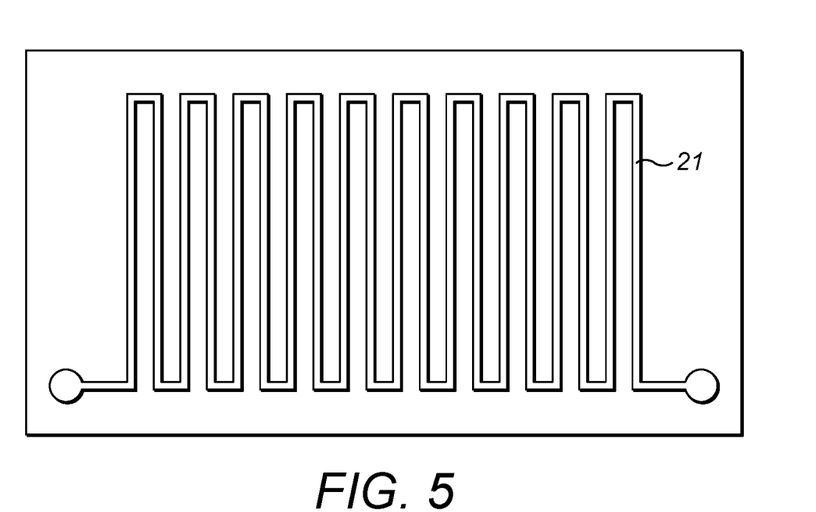
FIG. 5 is a plan view of a layer of a second example.
Figure 6:
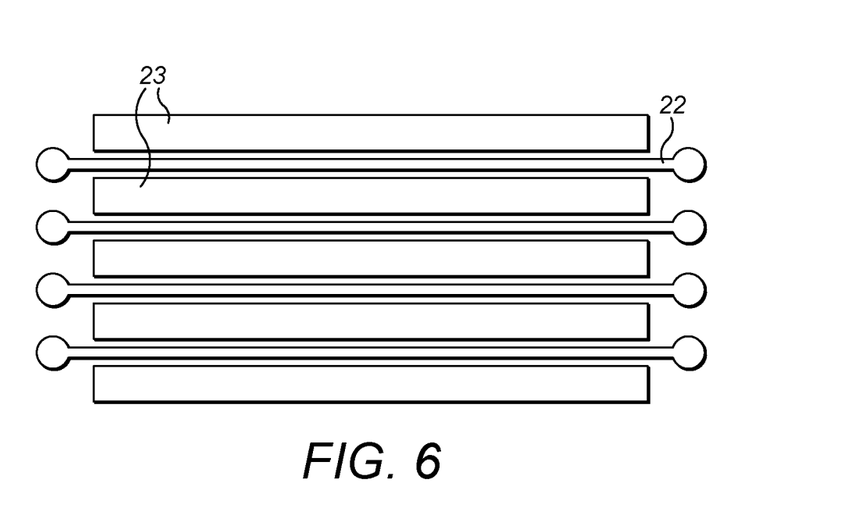
FIG. 6 is a schematic plan view of the other layer not shown in FIG. 5.
Figure 7:
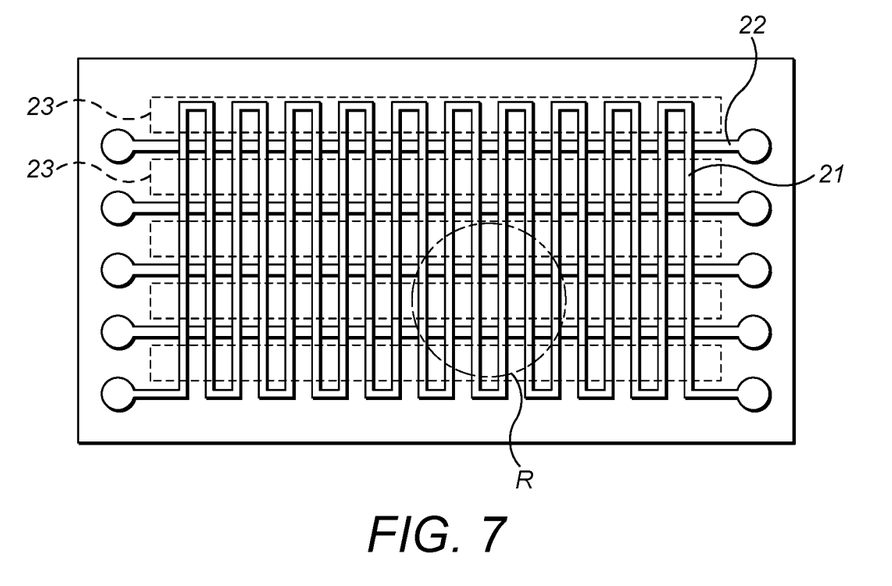
FIG. 7 is a schematic plan view with detail removed showing FIGS. 5 and 6 superimposed into a finished sensor.

A second example is shown in FIGS. 5 to 7. In this case, the first conductive ink track is a single grounded sinuous track 21 provided on the pad without the protrusions. The second conductive ink track 22 is formed as a number of discreet paths with a voltage connected across each which extend along between adjacent protrusions 23. The overlap between the two layers is illustrated in FIG. 7 from which the plurality of crossover points are apparent.

With reference to FIG. 7, if an impact is received over the region R, the bottom two tracks 22 will be forced into contact with the grounded track 21 such that the sensor will register an impact on the bottom two tracks. As configured here, the sensor is unable to determine where along the tracks 22 the impact was received, only that these are the two tracks which received the impact. If greater precision is required, each of the tracks 22 can be split into a number of short discreet sections each of which can separately register an impact. A relatively slight impact will provide a smaller contact area between the tracks 21, 22. On the other hand, a harder impact will provide a larger contact area. This affects the voltage connected across each of the tracks 22 such that the sensor is able to determine the magnitude of the impact force.

Figure 8:
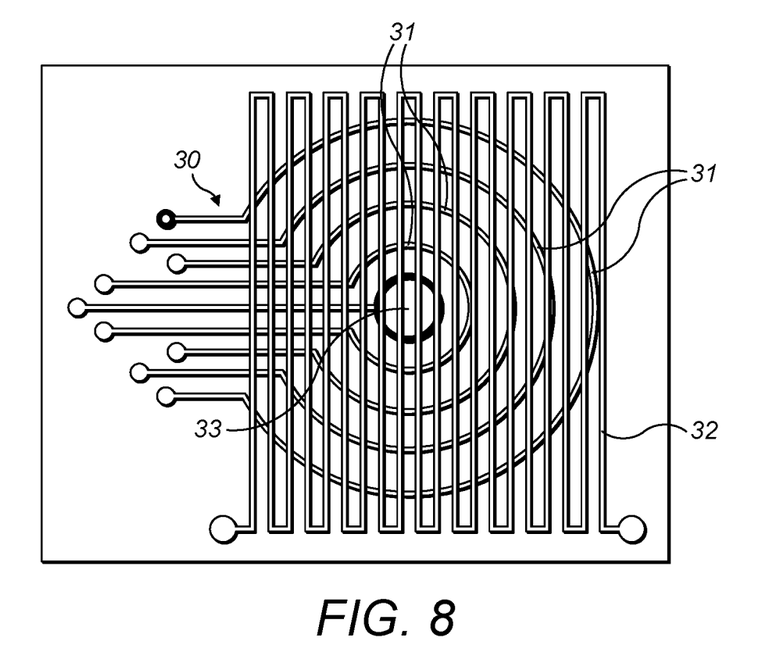
FIG. 8 is a view similar to FIG. 7 showing a third example of a sensor.

A further example is shown in FIG. 8. This shows that one of the conductive tracks 30 may now have a ring-like configuration. In this case, there are four discreet and generally concentric loops 31 each terminating at their own connectors forming one of the conductive tracks. A single central sensor 33 is also provided within the innermost loop 31. The second conductive track 32 is a single grounded sinuous track similar to that shown in FIG. 5. The protrusions are not shown in FIG. 8, but these are preferably elongate elements between adjacent runs of the sinuous track 32. They could equally be configured to fit between the loops 31, but this requires more complex construction.

As with the previous example, each of the conductive tracks 30 is able to independently sense that it has received an impact and to sense the magnitude of that impact. Therefore, again, the layout of the sensor should be configured according to the likely expected impact.

The garment to which the previously described sensor can be applied will now be described with reference to FIGS. 9A to D and FIG. 10.

FIGS. 9A to D show a padded top which is a type of padded underlayer intended for use by a rugby player. As described elsewhere in this application, the invention is applicable to wearable garments in general where impact protection is required. Whilst the top illustrated in FIGS. 9A to D is being used as an illustration, it will be readily understood that, for other such garments, the impact absorbing pads are placed in the areas most likely to receive an impact.

Figure 9A:
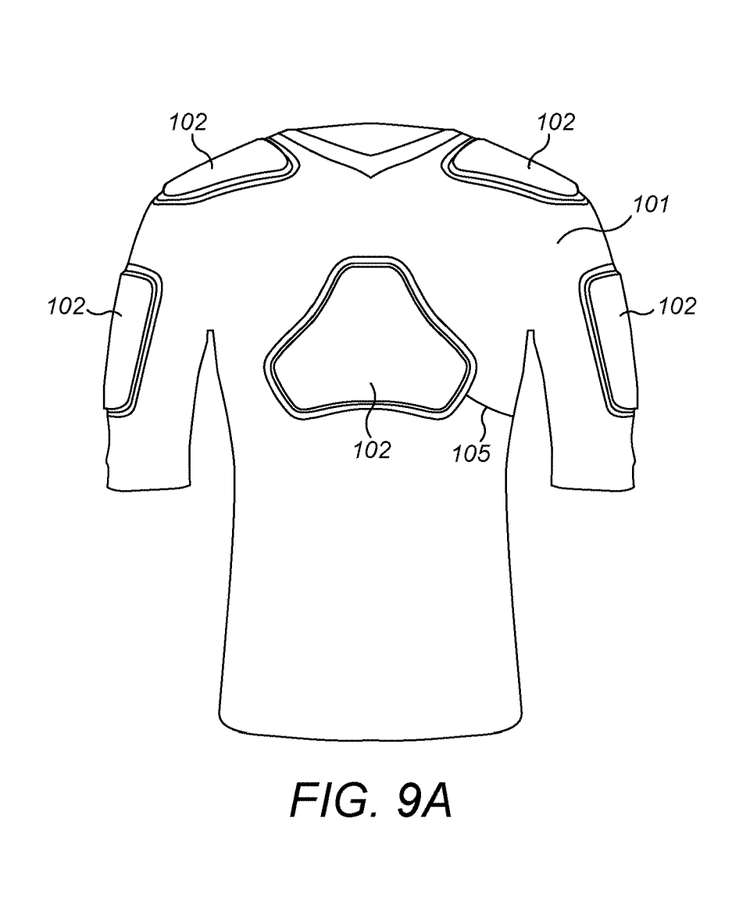
FIG. 9A is a front view of a garment according to a second aspect of the present invention.
Figure 9B:
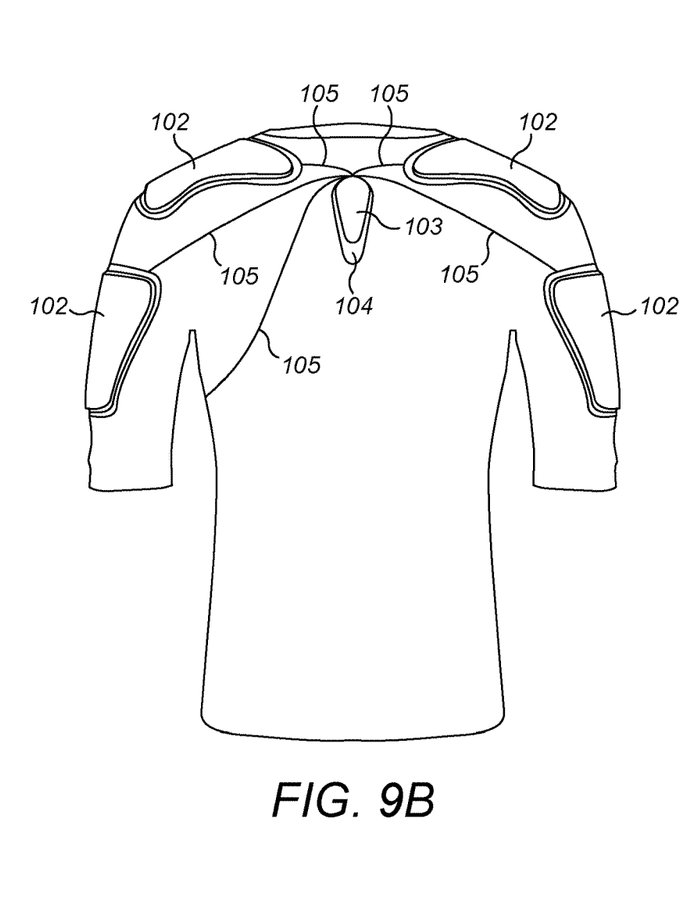
FIG. 9B is a back view of the garment of FIG. 9A.
Figure 9C:
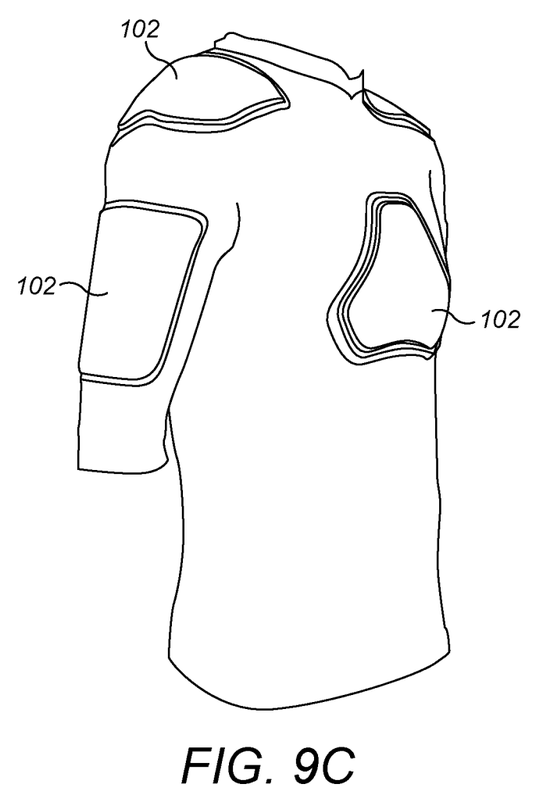
FIG. 9C is a perspective view of the garment of FIGS. 9A and 9B.
Figure 9D:
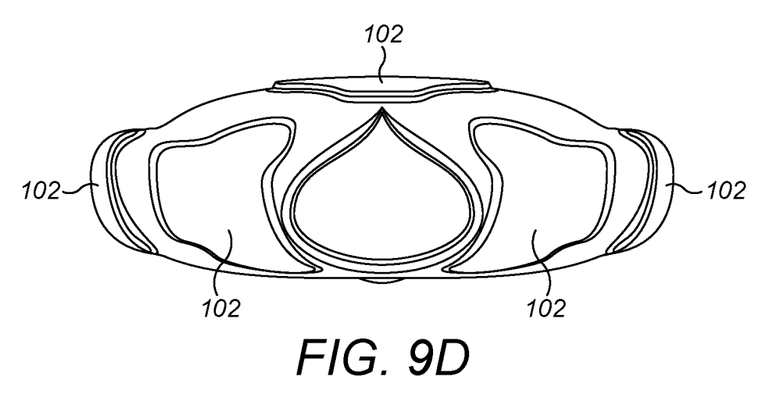
FIG. 9D is a top view of the garment of FIGS. 9A to 9C.

As shown in FIGS. 9A to C, the garment 101 comprises five impact absorbing pads 102 comprising a pair of shoulder pads, a pair of upper arm pads and a chest pad. Towards the upper part of the back of the garment 101 is a control module 103. This is surrounded by a soft layer 104 to provide comfort for the person wearing the garment as well as anyone impacting on them. The control module 103 is connected via an electrically conductive line 105 to each of the pads 102. The line 105 may simply be a wire which is retained between layers of the garment so that it does not impede the wearer.

The number and positioning of pads is provided as one example only. There may be fewer pads, for example just the shoulder pads, or additional pads, such as pads which protect the ribs.

Figure 10:
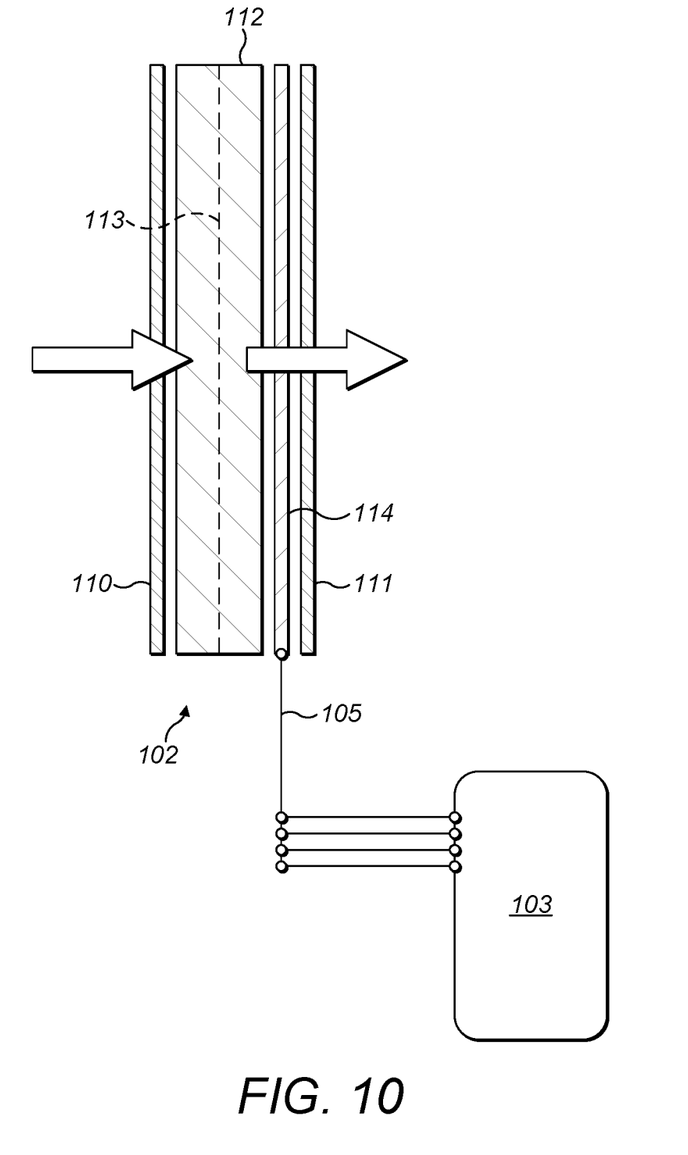
FIG. 10 is a schematic cross-section through various layers of a pad incorporating the sensor of the first aspect of the invention.

FIG. 10 shows the structure of the pad 102 in greater detail. The pad is sandwiched between an outer fabric layer 110 and an inner fabric layer 111. The pad consists of an impact absorbing layer 112. This may be made of a material such as foamed elastomers, thermoplastic elastomers, foamed thermoplastic elastomers or any suitable compliant material. This layer 112 will generally be less than 100 mm thick, more preferably less than 50 mm thick and most preferably less than 20 mm thick. Within the impact absorbing material 112 is an impact dissipating layer 113. This is an optional layer. This may be embedded in the impact absorbing material at the point of manufacture. Alternatively, the impact absorbing material 112 may be formed of two parts which are sandwiched around the impact dissipating layer 113. The impact dissipating layer 113 may be high impact engineering polymers (such as polycarbonate or nylon), glass or carbon fibre composites, bi-axial oriented films or any other material which provides high flexural strength, high puncture resistance and flexibility.

Between the impact absorbing material 112 and the inner fabric layer 111 is the sensor of FIGS. 3 to 8.

What is claimed is:

1. A sensor pad comprising a first layer of padding material having an inner face and a second layer of padding material having an inner face, the inner faces of the two layers of padding material facing one another; the inner face of the first layer of padding material being provided with a first printed conductive ink track; the inner face of the second layer of padding material being provided with a second printed conductive ink track; wherein at least one of the printed conductive ink tracks passes across the sensor pad in a number of runs at a plurality of spaced locations, the first printed conductive ink track on the first layer of padding material intersecting at a plurality of locations with the second printed conductive track on the second layer of padding material; at least one of the layers of padding material being provided on its inner face with a plurality of raised portions arranged over the inner face of the layer of padding material between adjacent runs of the printed conductive ink track and facing the inner face of the other layer of padding material to maintain the two printed conductive ink tracks apart when the sensor pad is unstressed, but which are compressible to deform to allow localised contact between the first printed conductive ink track and second printed conductive ink track when pressure is applied to the sensor pad.

2. A sensor pad according to claim 1, wherein at least one of the printed conductive ink tracks comprises a plurality of discreet tracks.

3. A sensor pad according to claim 1, wherein at least one of the printed conductive ink tracks has a single sinuous path.

4. A sensor pad according to claim 1, further comprising an impact absorbing layer provided on one side of the sensor pad.

5. A sensor pad according to claim 4, further comprising an impact dissipating layer within the impact absorbing layer.

6. A wearable garment comprising a garment including at least one sensor pad; wherein the at least one sensor pad comprises: a first layer of padding material having an inner face and a second layer of padding material having an inner face, the inner faces of the two layers of padding material facing one another; the inner face of the first layer of padding material being provided with a first printed conductive ink track; the inner face of the second layer of padding material being provided with a second printed conductive ink track: wherein at least one of the printed conductive ink tracks passes across the sensor pad in a number of runs at a plurality of spaced locations, the first printed conductive ink track on the first layer of padding material intersecting at a plurality of locations with the second printed conductive track on the second layer of padding material; at least one of the layers of padding material being provided on its inner face with a plurality of raised portions arranged over the inner face of the layer of padding material between adjacent runs of the printed conductive ink track and facing the inner face of the other layer of padding material to maintain the two printed conductive ink tracks apart when the at least one sensor pad is unstressed, but which are compressible to deform to allow localised contact between the first printed conductive ink track and second printed conductive ink track when pressure is applied to the at least one sensor pad.

* * * * *